United States Patent
Snell

Patent Number: 5,456,691
Date of Patent: Oct. 10, 1995

[54] PROGRAMMING SYSTEM HAVING MULTIPLE PROGRAM MODULES

[75] Inventor: Jeffery D. Snell, Northridge, Calif.

[73] Assignee: Pacesetter, Inc., Sylmar, Calif.

[21] Appl. No.: 152,999

[22] Filed: Nov. 12, 1993

[51] Int. Cl.⁶ .................................................. A61N 1/36
[52] U.S. Cl. ................................................ 607/30
[58] Field of Search ........................ 607/30, 31, 32

[56] References Cited

U.S. PATENT DOCUMENTS

| | | |
|---|---|---|
| 4,024,875 | 5/1977 | Putzke . |
| 4,049,004 | 9/1977 | Walters . |
| 4,066,086 | 1/1978 | Alferness et al. . |
| 4,232,679 | 11/1980 | Schulman . |
| 4,809,697 | 3/1989 | Causey, III et al. . |
| 4,846,180 | 7/1989 | Buffet ........................... 607/30 |
| 4,867,163 | 9/1989 | Schaldach ...................... 607/30 |
| 4,958,632 | 9/1990 | Duggan . |
| B1 4,066,086 | 6/1984 | Alferness et al. . |
| B1 4,232,679 | 5/1988 | Schulman . |

*Primary Examiner*—William E. Kamm
*Assistant Examiner*—Scott M. Getzow
*Attorney, Agent, or Firm*—Harold C. Schloss

[57] ABSTRACT

A programming system is provided in which a control program for an implantable medical device is constructed from program modules that are selected by a physician. Only the selected modules are loaded into the memory of the implantable medical device, each one of which provides the control functions necessary to provide a different therapy or diagnostic function. Because a physician typically does not need to elect all of the available therapies or diagnostic routines, the resulting control program may be smaller than a general purpose program designed to implement all of the possible treatments to a patient. Further, a greater selection of therapies and diagnostic routines may be provided, without necessitating an increase in the memory capacity of the implantable medical device.

39 Claims, 4 Drawing Sheets

PROGRAMMING SYSTEM HAVING MULTIPLE PROGRAM MODULES

BACKGROUND OF THE INVENTION

This invention relates to implantable medical devices, and more particularly, to programming systems for providing implantable medical devices with control programs based on multiple program modules.

Implantable medical devices such as cardiac simulating devices, drug pumps, cochlear implants, and neurostimulators perform a variety of complex medical functions. For example, a cardiac stimulating device may detect various cardiac abnormalities and provide corresponding corrective therapies to a patient's heart. A cardiac stimulating device may also use diagnostic routines to monitor a patient's condition. Typically, cardiac stimulating devices such as pacemakers contain microprocessor-based control circuitry to implement the complex therapies and diagnostic routines that are used. Consequently, a control program is usually required to operate this type of device.

Cardiac stimulating devices generally contain a dedicated control circuit to provide the most basic, life-sustaining pacing functions. More complex functions are handled by executing the control program. For example, the control program is used to determine whether a cardioversion or defibrillation shock should be applied to a patient's heart. However, certain functions are of interest only to those patients who suffer from specific conditions. For example, if a patient suffers from tachycardia, a condition in which the heart beats too quickly, a diagnostic module that measures and stores data related to tachycardia can be used. However, this function would most likely not be used by a patient who does not experience tachycardia episodes. Similarly, the ability of a control program to generate an antitachycardia therapy in response to a detected antitachycardia episode is only useful for patients who suffer occurrences of tachycardia.

Typically, however, cardiac stimulating devices are designed to operate under the control of a single control program. Although certain parameters may be adjusted, such as the base pacing rate, the control program itself is not altered by the physician. If a feature that the control program provides is not required, the physician disengages that function, so that it is not used. For example, U.S. Pat. No. 4,958,632 (Duggan) shows a pacemaker with multiple functions that may be selected by a physician. However, the number of features that may be readily provided by the pacemaker in the Duggan patent is limited by the capacity of the memory within that device. Further, because the instructions used to provide each feature remain loaded in the memory of the device, even if a feature is not used, the memory reserved for that feature cannot be used to provide a different function. Although more memory could be provided, increasing the size of the memory is undesirable, because additional memory consumes more power and when a cardiac stimulating device's battery is exhausted the device must be surgically replaced.

SUMMARY OF THE INVENTION

Therefore, in accordance with the present invention, a control program for an implantable medical device such as a cardiac stimulating device is provided that can be constructed by a physician or trained specialist from individual program modules, each providing the control necessary to implement a single device function. Because a physician does not need to elect all of the available functions, the resulting control program is smaller than a general purpose program designed to implement all potentially useful device functions. Further, a greater selection of therapies and diagnostic routines may be provided, without necessitating an increase in the memory capacity of the device.

The modules can either be individually loaded into an implantable medical device such as a cardiac stimulating device, or can be combined and loaded as a single control program. If the modules are loaded separately, they can be placed in predetermined slots in memory or, alternatively, loaded at consecutive memory locations. Individual memory modules can be invoked when necessary by a root module or can be accessed by a function call from a root module. A root module may also be used to moderate communications between the separate modules. Further, modules may pass control from one to the next without using a root module. If a root module is provided in read-only memory (ROM), flags within the memory of the cardiac stimulating device may be set to indicate the memory locations of the program modules.

An apparatus is therefore provided which provides control of an implantable medical device that contains memory. The apparatus has circuitry for selecting, according to patient needs, a subset of program modules from a group of distinct program modules. The apparatus also has circuitry for loading the subset of program modules into the memory of the implantable medical device. The subset provides control of the operation of the implantable medical device for satisfying the patient needs.

A method for controlling the operation of an implantable medical device that contains memory into which software can be loaded is also provided. The method involves selecting a subset of program modules from a group of distinct program modules according to patient needs. The method also involves loading the subset of program modules into the memory of the implantable medical device. The subset of program modules provides control of the operation of the implantable medical device for satisfying the patient needs.

A cardiac stimulating device is also provided that has memory into which software may be loaded. The cardiac stimulating device has circuitry for receiving a subset of cardiac program modules. The subset is selected from a group of distinct cardiac program modules according to patient needs. The cardiac stimulating device also has circuitry for storing the subset of cardiac program modules in the memory of the cardiac stimulating device. The subset of cardiac program modules provides control of the operation of the cardiac stimulating device for satisfying the patient needs.

A programming system is also provided that has an implantable medical device and a programmer. The implantable medical device, which may be implanted in the body of a patient, has first and second sensors for measuring first and second data signals. The implantable medical device also has memory for storing the first and second data signals. A control unit within the implantable medical device is used for allocating a portion of the memory to be used for storing the first data signals and a portion of the memory to be used for storing the second data signals. The programmer has an input interface for receiving commands to allocate the memory within the implantable medical device. The programmer also has circuitry for generating allocation signals in response to the commands and a telemetry head for transmitting the allocation signals to the implantable medical device. The control unit within the implantable medical device contains circuitry for receiving the allocation signals. The control unit allocates the memory to the first and second data signals in response to the allocation signals.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENTS

Figure 1:
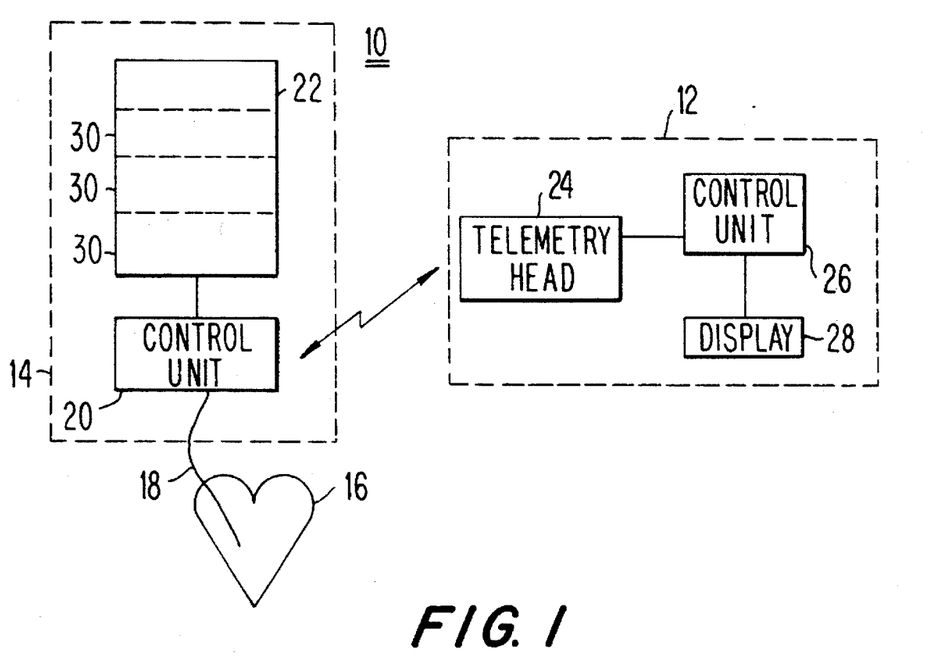
FIG. 1 is a schematic diagram of a programming system in accordance with the present invention, in which a subset of selected program modules is provided to an implantable medical device.

In accordance with the present invention, a programming system 10 is provided that is made up of both a programmer 12 and an implantable medical device, which could be, for example, a cardiac stimulating device 14, as shown in FIG. 1. The cardiac stimulating device 14 applies electrical stimulation to a patient's heart 16 using a lead 18. A control unit 20 preferably contains a microprocessor for executing program modules that have been selected by a physician to suit a patient's particular needs. Dedicated control circuitry contained within the control unit 20 can also be used to provide control of the cardiac stimulating device 14, in place of a microprocessor. The control unit 20 implements the instructions loaded in the memory 22. These instructions may be loaded into the cardiac stimulating device 14 by the programmer 12 via a telemetry head 24. The programmer 12 also contains a control unit 26 and a display 28.

Figure 2:
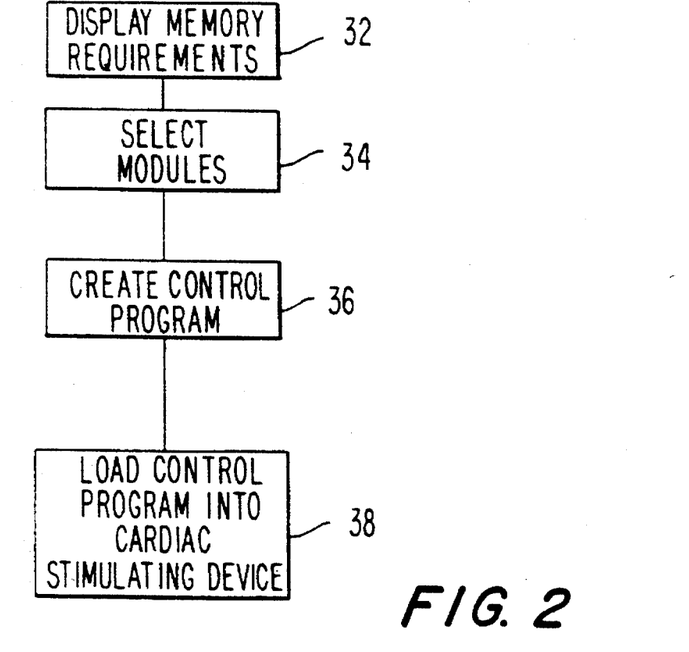
FIG. 2 is a schematic diagram of a procedure for selection of the desired program modules according to the present invention, in which the programmer creates a control program using the selected modules.
Figure 3:
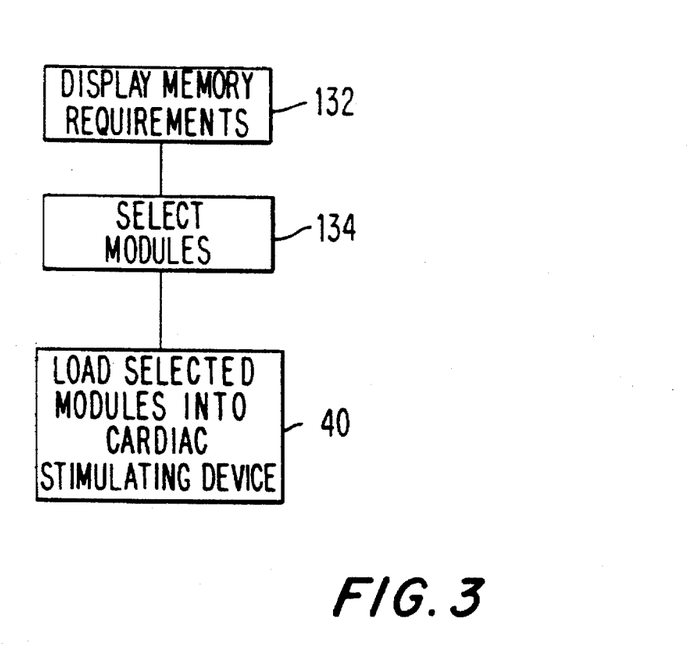
FIG. 3 is a schematic diagram of a procedure for program module selection according to the present invention, in which the modules are separately loaded into the memory of an implantable medical device.

The programming system uses multiple cardiac program modules 30 within the cardiac stimulating device 14. Because program modules vary in size, the programming system 10 preferably displays the memory requirements of each module on display 28 at step 32, as shown in FIG. 2 and at step 132, as shown in FIG. 3, which allows the physician to make an informed decision when balancing the benefits of different therapies and diagnostic routines. The amount of memory that is available in the cardiac stimulating device is also displayed. The memory requirements of the modules and the available memory in the cardiac stimulating device 14 can be displayed either numerically or graphically, using, for example, a pie chart. Alternatively, to simplify operation of the system, the memory requirements of the modules and the memory capacity of the cardiac stimulating devices can be hidden, so that this information is only available at the request of the user.

The physician selects program modules corresponding to those therapies and diagnostic routines that are thought to be the most effective for treating the patient at step 34, as shown in FIG. 2 and at step 134, as shown in FIG. 3. The actual selection may be made using any convenient user interface, such as a keyboard, lightpen or mouse. The physician can select the desired modules from a menu that is displayed on the programmer's display 28. As the physician selects specific modules, the selections can be highlighted, and if a pie chart or other memory utilization display is used, the chart or display can be updated to reflect the amount of memory that remains available.

As shown in FIG. 2, the modules are combined by the programmer 12 (FIG. 1) to create the cardiac 10 stimulating device control program at step 36. The control program for the cardiac stimulating device can be created by running linking software on the programmer. Alternatively, other equally suitable methods of providing an executable control program can be used. For example, the selected program modules could be merged together and subsequently compiled, rather than combining compiled object modules using a linker. Further, a custom routine can be used to combine the program modules into an executable program. Regardless of how the control program is created at step 36, the programmer 12 (FIG. 1) next loads the executable control program into the cardiac stimulating device at step 38. Either the entire program or specific portions of the program may be loaded. For example, it may be desired to clear the entire memory 22 (FIG. 1). In that case, all non-zero portions of the program could be loaded into the cleared memory 22. Alternatively, if only some of the program was modified, a smaller portion of the memory 22 might be cleared. Only the non-zero portions of the control program corresponding to the smaller portion of the memory 22 would then be loaded. Further, the memory need not be cleared before loading the program, because the existing data in the memory 22 may be directly replaced by the program data.

Referring to FIG. 1, loading may be initiated by using the programmer 12 to telemeter an appropriate loading command to the cardiac stimulating device 14. The control unit 20 contains telemetry circuitry for receiving and interpreting loading commands. If a command is received to begin loading the control program, further signals that are received by the cardiac stimulating device 14 are directed to the memory 22. For example, the loading command may contain a code which instructs circuitry within the control unit 20 to write a specified quantity of incoming signals to a particular memory address.

Alternatively, the control program can be loaded using a series of packets, each of which contains a target memory address, program data corresponding to a portion of the program to be loaded, and a command instructing the control unit 20 to store the program data at the target address. In any event, while the control program is being loaded, dedicated control circuitry contained within the cardiac stimulating device 14 performs basic pacing functions, although the control unit 20 does not execute the control program until the loading process is complete.

Another method of loading the control program into the memory 22 involves telemetering a reset command to the cardiac stimulating device 14, which causes the cardiac stimulating device to "reboot," by loading instructions from boot ROM in control unit 20 into memory 22. These instructions direct the cardiac stimulating device 14 to receive the control program code via telemetry. During loading of the control program, the control unit 20 does not execute the instructions in memory 22. However, dedicated control circuitry contained within control unit 20 continues to provide the patient with basic pacing functions. After the control program has been loaded into memory 22, the cardiac stimulating device 14 provides the selected therapies to the patient as needed.

Figure 4:
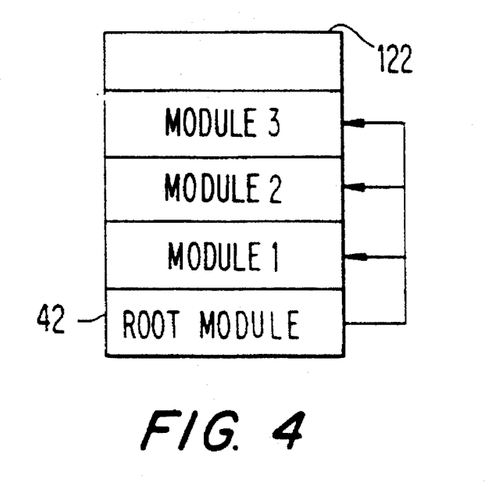
FIG. 4 is a schematic diagram of the memory of an implantable medical device into which separate program modules have been loaded, such that a root module can invoke the desired modules as needed, in accordance with the present invention.
Figure 5:
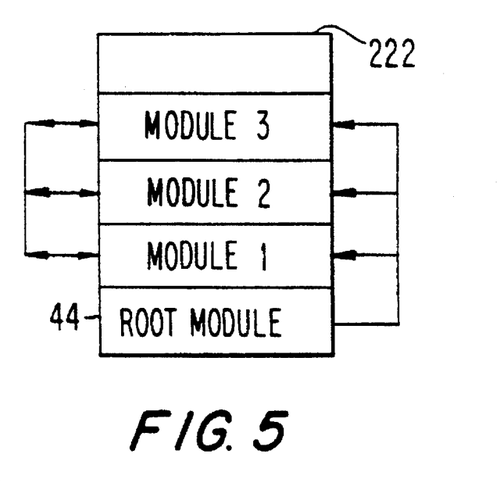
FIG. 5 is a schematic diagram of the memory of an implantable medical device into which separate program modules have been loaded, such that a root module can moderate communications between modules, in accordance with the present invention.
Figure 6:
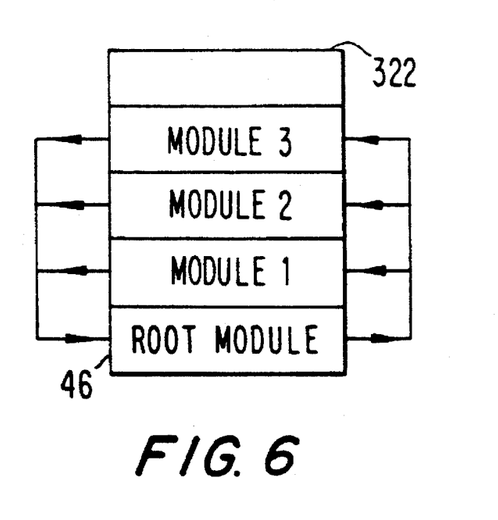
FIG. 6 is a schematic diagram of the memory of an implantable medical device into which separate program modules have been loaded, such that a root module can make function calls to the program modules, in accordance with the present invention.

As shown in FIG. 3, after displaying the memory requirements at step 132, and after the physician has selected the desired therapies at step 134, the programmer may also load the selected program modules individually into the cardiac stimulating device at step 40, rather than loading an executable control program. FIGS. 4–6 are schematic diagrams of the memory of the cardiac stimulating device in which the program modules 35 have been loaded. The number of program modules that can be loaded into the device depends on the size of the modules and the amount of available device memory. In FIGS. 4–6, three program modules and a root module have been loaded. The root module contains instructions that allow the program modules to control the cardiac stimulating device during operation. For example, the root module may use a table in which various selected parameters are stored, such as the number and types of program modules that have been selected. The arrows in FIGS. 4–6 represent the general direction of the flow of control between modules.

One possible configuration of the root module and the program modules is shown in a memory 122 in FIG. 4. During operation, the root module 42 invokes the appropriate program modules according to a preprogrammed hierarchy. For example, a patient's physician might select both a diagnostic program module and antitachycardia program module. Initially, the root module 42 invokes the diagnostic module, so that the cardiac stimulating device 14 (FIG. 1) measures and stores the signals received from various sensors. During the diagnostic routine, the patient's cardiac condition is monitored, so that if the patient experiences an episode of tachycardia, the root module 42 can invoke the antitachycardia module. When the tachycardia episode has been successfully terminated, the root module 42 invokes the diagnostic module again.

Another possible arrangement of program modules in a memory 222 is shown in FIG. 5. In contrast with the approach shown in FIG. 4, the root module 44 does not assume control of the cardiac stimulating device 14 (FIG. 10), but merely facilitates communication between respective modules. Control of the cardiac stimulating device 14 (FIG. 1) passes from one program module to the next as determined by the instructions within each of those modules.

An approach similar to the one shown in FIG. 4 is shown in FIG. 6. The memory 322 contains the root module 46, which retains primary control of the cardiac stimulating device 14 (FIG. 1). Unlike the arrangement shown FIG. 4, however, the root module 46 in FIG. 6 does not relinquish control to an invoked program module, but rather makes function calls to the appropriate modules as necessary. An alternative approach is for the root module to invoke modules according to a predetermined schedule.

Figure 7:
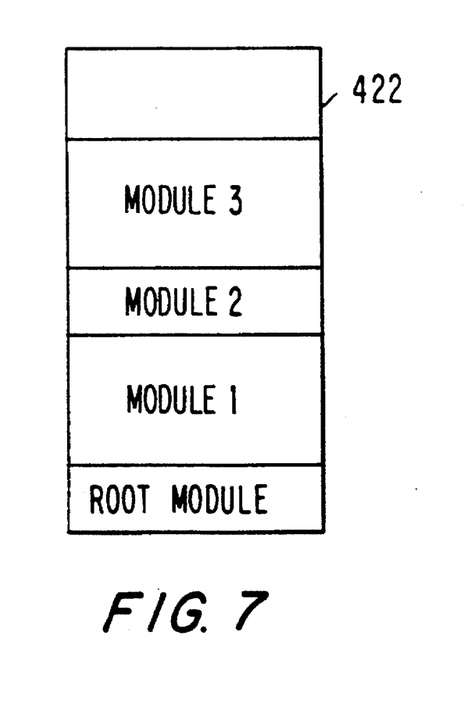
FIG. 7 is a schematic diagram of the memory of an implantable medical device into which separate program modules have been loaded, such that each module is allocated only as much memory as is required by that module, in accordance with the present invention.

The selection of which of the possible approaches to use is a design decision that is influenced by many factors, including the amount of memory that is available in the device, ease of programming, and the specific hardware features present in each device. Further, the selected subset of cardiac program modules does not need to be loaded into memory at evenly spaced address locations or slots, as shown in FIGS. 4–6. Rather, each module may be allocated only as much memory as is needed. For example, as shown in FIG. 7, module 1 requires more of the memory 422 than module 2, so that module 1 uses more memory than module 2. Although this technique is not as simple as using fixed memory slots, it is more efficient, because the entire memory is used.

Figure 8:
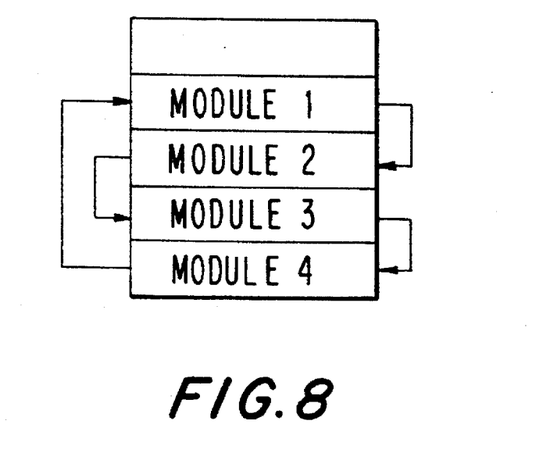
FIG. 8 is a schematic diagram of the memory of an implantable medical device into which program modules have been loaded, such that after each module performs its function, it passes control to the next, in accordance with the present invention.

Modules can also be configured so that after each module performs its function it passes control to another module. For example, a first diagnostic module could be used to record the measured heart rate. After recording the rate, the first module could pass control to a second diagnostic module that monitors and records the signals measured by one of various other sensors. As shown in FIG. 8, upon completion of its function, module 1 passes control to module 2, which in turn passes control to module 3, and so forth. With this arrangement, a root module is not required.

Figure 9:
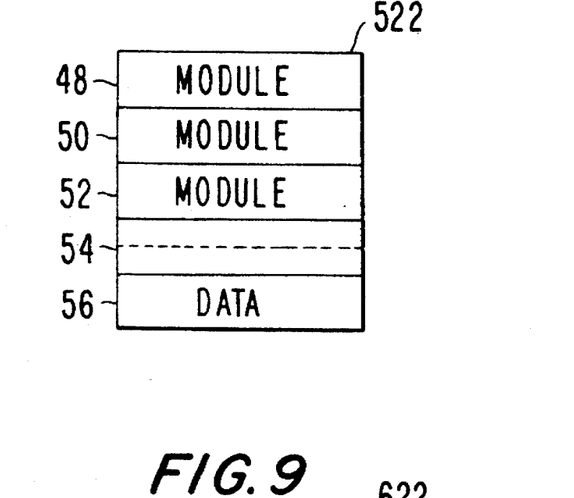
FIG. 9 is a schematic diagram of the memory of an implantable medical device into which program modules and data have been loaded, in accordance with the invention.

If it is desired to store a root module in ROM, a set of registers or a portion of memory may be used to store a series of flags, which indicate where selected modules have been loaded into memory. For example, if memory 522 is divided into five segments, as shown in FIG. 9, the flags may be used to indicate whether a module is stored in a particular segment. Therefore, if modules were loaded into segments 48 and 50, the flags corresponding to those segments would be set to show that segments 48 and 50 contain executable instructions. If a module fills segment 52 completely and partially fills segment 54, then the flag corresponding to segment 52 would be set to show that segment 52 may be executed, whereas the flag corresponding to segment 54 would be set to indicate that segment 54 should not be executed, because it only contains a portion of a module. Similarly, if segment 56 contains data, the corresponding flag can be set to show that no executable instructions are present. The instructions for setting the flags are transmitted via telemetry when the modules are loaded into memory 522.

Regardless of what type of memory allocation scheme is used, after the modules have been loaded into the memory, error checking is preferably performed to ensure that the modules are loaded correctly. For example, even if the physician makes only minor changes in a previously prescribed set of therapies, the entire set of selected program modules or a portion of these modules can be retransmitted to the cardiac stimulating device 14 (FIG. 1). Alternatively, the device memory 22 (FIG. 1) can be tested to ensure each of the desired modules is present.

Figure 10:
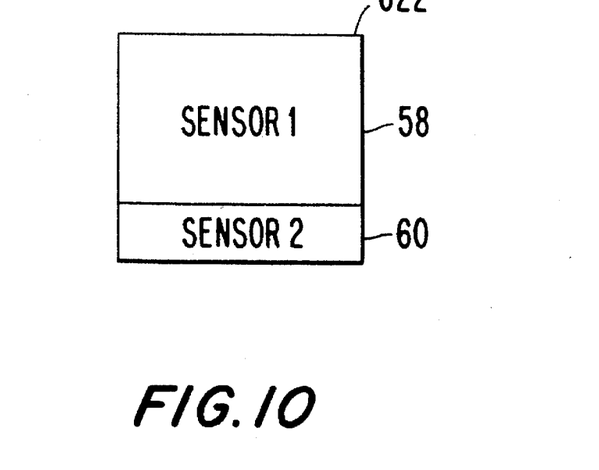
FIG. 10 is a schematic diagram of the memory of an implantable medical device in which two sets of sensor data have been stored.

As described previously, an implantable medical device does not require a microprocessor. For example, a cardiac stimulating device 14 (FIG. 1) may use dedicated control circuitry to provide all of the necessary device functions. Cardiac stimulating devices such as these often contain a buffer for recording the time intervals between sensed cardiac events. In accordance with the present invention, it is also possible to store additional data, such as measurements made by motion sensors. Regardless of whether or not a microprocessor is used, if several sets of data are stored, a physician may often desire to focus on a particular set. For example, if a patient experiences discomfort that the physician believes is related to the response of the cardiac stimulating device to the magnitude of the signals measured by the motion sensor, the physician may wish to measure these signals more frequently and over a longer time period than would otherwise be the case. FIG. 10 shows a region of memory 622 that has been selectively configured by the physician into a larger segment 58, which is dedicated to storing data from sensor 1 in detail, and a smaller segment 60 for storing the data from sensor 2. Memory 622 may therefore be allocated by the control unit (as in FIG. 1) in the same way that memory 422 (FIG. 7) is segmented based on the memory requirement of the various program modules.

Although the invention has been described primarily in the context of cardiac stimulating devices, it will be appreciated that the invention is not so limited. For example, the operation of implantable drug pumps, cochlear implants, and implantable neurostimulators can also be enhanced in accordance with the present invention.

Implantable drug pumps deliver drugs to patients on a predetermined schedule or when a sensor indicates that a patient needs a dose. Drug pumps such as these typically contain control circuitry and memory. Various drug delivery functions are provided by executing a control program. As with cardiac patients, each patient's individual condition differs. Depending on the specific drug that is delivered and the patient's lifestyle, drug pumps must provide different features. In accordance with the present invention, a control program is provided that is based on multiple program modules. Program modules can be selected by a physician to suit each individual patient. Because only a subset of the available modules is selected, the physician is able to choose from a wide range of drug therapy options without exceeding the memory capacity of the implantable drug pump.

Cochlear implants sense sound and provide corresponding electrical signals to stimulate a patient's nerves. A variety of signal processing techniques can be used to convert the sound signal into the stimulation signals. However, because cochlear implants have limited memory, it has typically not been possible to implement all of the desired techniques. In accordance with the present invention, a cochlear implant control program is based on multiple program modules. The physician may therefore select from numerous signal processing routines, which would otherwise not be available. Further, the physician may test various modules to determine the best combination of signal processing techniques for an individual patient.

Implantable neurostimulators represent an additional class of implantable medical device that can be improved in accordance with the present invention by using multiple program modules. Implantable neurostimulators are often used to block pain by electrically stimulating nerves with a series of electrical pulses. Pulse width and amplitude vary widely. Further, it may be desirable to provide the pulses in a variable length burst. The various functions related to pulse generation can each be provided by a separate module. It is also possible to provide a program module to receive readings from various implanted sensors. As with the other types of implantable medical devices, neurostimulating devices have limited memory capacity. Therefore, the use of multiple program modules allows a physician to select from a wider range of options than if a single control program were used.

It will be understood that the foregoing is merely illustrative of the principles of this invention, and that various modifications can be made by those skilled in the art without departing from the scope and spirit of the invention.

What is claimed is:

1. A programmer for providing control of an implantable medical device, said implantable medical device having a memory and means for controlling operation of the implantable medical device in accordance with a control program stored in the memory, said programmer comprising:

means for selecting a subset of program modules from a plurality of distinct program modules;

means for creating a control program from the selected subset of program modules; and means for downloading the control program from the programmer into the memory of the implantable medical device.

2. The programmer defined in claim 1, further comprising:

means for displaying the memory requirements of each of the program modules; and means for displaying the memory capacity of the implantable medical device.

3. The programmer defined in claim 1, wherein the means for creating the control program comprises a linker for linking the subset of program modules to create the control program.

4. The programmer defined in claim 1, wherein the means for creating the control program comprises:

means for merging the program modules; and means for compiling the merged modules to create the control program.

5. A programmer for providing control of an implantable medical device, as claimed in claim 1, further comprising:

means for determining the contents of the memory of the implantable medical device;

means for comparing the control program to the contents of the memory of the implantable medical device; and means for downloading only those portions of the control program that differ from the contents of the memory of the implantable medical device.

6. A programmer for providing control of an implantable medical device, said implantable medical device having a memory and means for controlling operation of the implantable medical device in accordance with program modules stored in the memory, said programmer comprising:

means for selecting a subset of program modules from a plurality of distinct program modules; and means for downloading each of the modules in the subset of program modules from the programmer into the memory of the implantable medical device separately.

7. The programmer defined in claim 7, further comprising means for downloading a root program module into the memory of the implantable medical device.

8. The programmer defined in claim 6, wherein each of the program modules is downloaded into a separate slot in the memory.

9. The programmer defined in claim 6, wherein the program modules are downloaded into memory such that only as much memory as is required by each program module is used.

10. A method for controlling the operation of an implantable medical device that contains memory, into which program modules can be downloaded, and a control unit that controls the operation of the implantable medical device in accordance with program modules in the memory, comprising the steps of:

selecting a subset of program modules from a set containing a plurality of distinct program modules;

creating a control program from the subset of program modules; and downloading the subset of program modules into the memory of the implantable medical device.

11. The method defined in claim 10, further comprising the step of displaying the memory requirements of each of the program modules.

12. The method defined in claim 10, further comprising the step of displaying the memory capacity of the implantable medical device.

13. The method defined in claim 10, further comprising the step of downloading the control program into the memory of the implantable medical device.

14. The method defined in claim 10, wherein the step of creating the control program comprises the step of linking the subset of program modules to create the control program.

15. The method defined in claim 10, wherein the step of creating the control program comprises the steps of:

merging the program modules; and compiling the merged modules to create the control program.

16. The method defined in claim 10, further comprising the step of downloading each of the modules in the subset of program modules into the memory of the implantable medical device separately.

17. The method defined in claim 16, further comprising the step of downloading each of the program modules into a separate slot in the memory.

18. The method defined in claim 10, wherein one of the program modules is a root program module.

19. The method defined in claim 10, further comprising the step of downloading the program modules into memory such that only as much memory as is required by each program module is used.

20. A medical system comprising:

a programmer comprising:

a plurality of cardiac program modules, means for selecting a subset of the cardiac program modules, and means for transmitting the selected subset of cardiac program modules to the cardiac stimulating device; and a cardiac stimulating device comprising:

a memory, means for receiving the transmitted selected subset of cardiac program modules, means for storing the received subset of cardiac program modules in the memory of the cardiac stimulating device, and control means for controlling the operation of the cardiac stimulating device in accordance with the cardiac program modules stored in the memory of the cardiac stimulating device.

21. The medical system defined in claim 20, wherein the cardiac stimulating device further comprises means for storing the cardiac program modules in the memory of the cardiac stimulating device as a control program.

22. The medical system defined in claim 20, wherein the cardiac stimulating device further comprises means for storing each of the modules in the subset of cardiac program modules in the memory of the cardiac stimulating device separately.

23. The medical system defined in claim 20, wherein the cardiac stimulating device further comprises means for storing a root cardiac program module.

24. The medical system defined in claim 20, wherein each of the cardiac program modules is stored in a separate slot in the memory of the cardiac stimulating device.

25. The medical system defined in claim 20, wherein the cardiac program modules are stored in the memory of the cardiac stimulating device such that only as much memory as is required by each cardiac program module is used.

26. A medical system comprising an implantable medical device and a programmer, wherein the implantable medical device comprises:

first sensor means for measuring first data signals, second sensor means for measuring second data signals, a memory for storing the first data signals and the second data signals, and a control unit for allocating a portion of the memory to be used for storing the first data signals and a portion of the memory to be used for storing the second data signals; and wherein the programmer comprises:

an input interface for receiving commands to allocate the memory within the implantable medical device, means for generating allocation signals in response to the commands, and a telemetry head for transmitting the allocation signals to the implantable medical device, wherein the control unit contains circuitry for receiving the allocation signals and the control unit allocates the memory within the implantable medical device for the first and second data signals in response to the allocation signals.

27. A programmer for providing control of an implantable medical device, said implantable medical device having a memory and means for controlling operation of the implantable medical device in accordance with program modules stored in the memory, said programmer comprising:

means for selecting a subset of program modules from a plurality of distinct program modules; and means for downloading the subset of program modules into the memory of the implantable medical device.

28. The programmer defined in claim 27, further comprising:

means for displaying the memory requirements of each of the program modules; and means for displaying the memory capacity of the implantable medical device.

29. The programmer defined in claim 27, further comprising means for creating a control program from the subset of program modules.

30. The programmer defined in claim 29, wherein the means for downloading comprises means for downloading the control program into the memory of the implantable medical device.

31. The programmer defined in claim 29, wherein the means for creating the control program comprises a linker for linking the subset of program modules to create the control program.

32. The programmer defined in claim 29, wherein the means for creating the control program comprises:

means for merging the program modules; and means for compiling the merged modules to create the control program.

33. The programmer defined in claim 27, further comprising means for downloading each of the modules in the subset of program modules into the memory of the implantable medical device separately.

34. The programmer defined in claim 33, further comprising means for downloading a root program module into the memory of the implantable medical device.

35. The programmer defined in claim 33, wherein each of the program modules is downloaded into a separate slot in the memory.

36. The programmer defined in claim 33, wherein the program modules are downloaded into memory such that only as much memory as is required by each program module is used.

37. A method for controlling the operation of an implantable medical device that contains memory, into which program modules can be downloaded, and a control unit that controls the operation of the implantable medical device in accordance with program modules in the memory, comprising the steps of:

selecting a subset of program modules from a set containing a plurality of program modules; and downloading the subset of program modules into the memory of the implantable medical device.

38. A method for controlling the operation of an implantable medical device that contains memory, into which program modules can be downloaded, and a control unit that controls the operation of the implantable medical device in accordance with program modules in the memory, comprising the steps of:

selecting a subset of program module from a set containing a plurality of distinct program modules;

creating a control program from the subset of program modules; and downloading the control program into the memory of the implantable medical device.

39. A method for controlling the operation of an implantable medical device that contains memory, into which program modules can be downloaded, and a control unit that controls the operation of the implantable medical device in accordance with program modules in the memory, comprising the steps of:

selecting a subset of program module from a set containing a plurality of distinct program modules;

creating a control program from the subset of program modules;

determining the contents of the memory of the implantable medical device;

comparing the contents of the memory of the implantable medical device to the control program; and downloading, into the memory of the implantable medical device, the portions of the control program that differ from the contents of the memory of the implantable medical device.

\* \* \* \* \*